United States Patent
Ohyabu et al.

(10) Patent No.: US 10,815,393 B2
(45) Date of Patent: Oct. 27, 2020

(54) GELATIN, CHEMICALLY MODIFIED PRODUCT THEREOF, AQUEOUS COMPOSITION AND MEDICAL LAMINATE CONTAINING SAME, PRODUCTION METHOD FOR MEDICAL LAMINATE, AND CELL SHEET ISOLATION METHOD

(71) Applicants: Tokyo Metropolitan Industrial Technology Research Institute, Koto-ku, Tokyo (JP); NITTA GELATIN INC., Osaka-shi, Osaka (JP)

(72) Inventors: Yoshimi Ohyabu, Tokyo (JP); Shunji Yunoki, Tokyo (JP); Hirosuke Hatayama, Tokyo (JP); Masataka Ida, Yao (JP); Yosuke Hiraoka, Yao (JP)

(73) Assignees: TOKYO METROPOLITAN INDUSTRIAL TECHNOLOGY RESEARCH INSTITUTE, Tokyo (JP); NITTA GELATIN INC., Osaka-shi, Osaka (JP)

(*) Notice: Subject to any disclaimer, the term of this patent is extended or adjusted under 35 U.S.C. 154(b) by 73 days.

(21) Appl. No.: 15/769,362

(22) PCT Filed: Oct. 18, 2016

(86) PCT No.: PCT/JP2016/080829
§ 371 (c)(1),
(2) Date: Apr. 19, 2018

(87) PCT Pub. No.: WO2017/069116
PCT Pub. Date: Apr. 27, 2017

(65) Prior Publication Data
US 2018/0312726 A1    Nov. 1, 2018

(30) Foreign Application Priority Data
Oct. 21, 2015  (JP) ................. 2015-207399

(51) Int. Cl.
| C08H 1/06 | (2006.01) |
| C07K 14/78 | (2006.01) |
| A61L 15/32 | (2006.01) |
| C09H 3/00 | (2006.01) |
| C12M 3/04 | (2006.01) |
| A61L 27/34 | (2006.01) |
| A61L 27/26 | (2006.01) |
| A61L 27/38 | (2006.01) |
| A61L 15/40 | (2006.01) |
| A61L 27/52 | (2006.01) |
| A61L 15/22 | (2006.01) |
| A61L 27/22 | (2006.01) |
| A61L 27/54 | (2006.01) |
| A61L 27/60 | (2006.01) |
| C08L 89/06 | (2006.01) |
| C12M 1/12 | (2006.01) |

(52) U.S. Cl.
CPC .............. *C09H 3/00* (2013.01); *A61L 15/225* (2013.01); *A61L 15/32* (2013.01); *A61L 15/40* (2013.01); *A61L 27/222* (2013.01); *A61L 27/26* (2013.01); *A61L 27/34* (2013.01); *A61L 27/3804* (2013.01); *A61L 27/3813* (2013.01); *A61L 27/3839* (2013.01); *A61L 27/52* (2013.01); *A61L 27/54* (2013.01); *A61L 27/60* (2013.01); *C07K 14/78* (2013.01); *C08H 1/06* (2013.01); *C08L 89/06* (2013.01); *C12M 3/04* (2013.01); *C12M 25/00* (2013.01); *A61L 2430/34* (2013.01); *C08L 2201/54* (2013.01); *C08L 2203/02* (2013.01)

(58) Field of Classification Search
CPC .. C09H 3/00; A61L 15/32; C08H 1/06; C08L 89/06
See application file for complete search history.

(56) References Cited

U.S. PATENT DOCUMENTS

| 4,894,441 A | 1/1990 | Menicagli |
| 5,318,889 A | 6/1994 | Bagchi et al. |
| 5,919,906 A | 7/1999 | Rowlands et al. |
| 2007/0004034 A1 | 1/2007 | Bouwstra et al. |
| 2014/0186821 A1* | 7/2014 | Daum ............. C12Q 1/6806 435/5 |
| 2015/0239954 A1 | 8/2015 | Quan et al. |
| 2015/0374881 A1 | 12/2015 | Yamigami et al. |
| 2016/0121025 A1 | 5/2016 | Yamashita et al. |

FOREIGN PATENT DOCUMENTS

| JP | S64-006300 A | 1/1989 |
| JP | H08-143821 A | 6/1996 |
| JP | 2000-144059 A | 5/2000 |

(Continued)

OTHER PUBLICATIONS

Nakayama et al., "Poly(N-isopropylacrylamide)-based Smart Surfaces for Cell Sheet Tissue Engineering," Material Matters, vol. 5, No. 3, 2010, pp. 56-61 (in English and Japanese).
Ohyabu et al., "Evaluation of gelatin hydrogel as a potential carrier for cell transportation," Journal of Bioscience and Bioengineering, vol. 118, No. 1, 2014, pp. 112-115.
Decision to Grant Patent for Japanese Patent Application No. 2015-207399, dated Oct. 3, 2017 (in English and Japanese).
Notice of Grounds of Rejection for Japanese Patent Application No. 2015-207399, dated Jun. 6, 2017 (in English and Japanese).

(Continued)

*Primary Examiner* — Ruth A Davis
(74) *Attorney, Agent, or Firm* — Dickinson Wright PLLC (57) ABSTRACT

A gelatin or a chemically modified product thereof contains 10 to 50% by mass of a high-molecular weight component, and a low-molecular weight component in such an amount that a value obtained by subtracting a low-molecular weight component content from a high-molecular weight component content is greater than or equal to 0% by mass.

8 Claims, 4 Drawing Sheets

(56) References Cited

FOREIGN PATENT DOCUMENTS

| | | |
|---|---|---|
| JP | 2006-063100 A | 3/2006 |
| JP | 2006-511219 A | 4/2006 |
| JP | 2011-172925 A | 9/2011 |
| JP | 2014-100110 A | 6/2014 |
| JP | 2015-122985 A | 7/2015 |
| WO | 2014/104366 A1 | 3/2014 |
| WO | 2014/104366 A1 | 7/2014 |
| WO | 2014192909 A1 | 12/2014 |

OTHER PUBLICATIONS

Kanegae et al., "Ultrasonic Degradation of High Molecular Weight Components of Gelatin," The Journal of Photographic Science, vol. 40, No. 5 & 6, 1992, pp. 187-189.

Kanegae et al., "Ultrasonic Degradation Process of Fractionated Gelatin," The Journal of Photographic Science, vol. 41, No. 4, 1993, pp. 176-179.

European Search Report dated May 21, 2019, which issued in corresponding European Patent Application No. 16857430.9.

Claude A. Farrugia et al., "Comparison of the Molecular Weight Distribution of Gelatin Fractions by Size-Exclusion Chromatography and Light Scattering", Pharmacy and Pharmacology Communications, Dec. 1, 1998, pp. 559-562.

Valery Normand et al., "Gelation Kinetics of Gelatin: A Master Curve and Network Modeling", Macromolecules, vol. 33, No. 3, Feb. 1, 2000, pp. 1063-1071.

Nadia Elharfaoui et al., "Molecular Weight Influence on Gelatin Gels: Structure, Enthalpy and Rheology", Macromolecular Symposia, vol. 256, No. 1, Sep. 1, 2007, pp. 149-157.

WO 2014/192909 A1, US 2016/0121025 A1.

* cited by examiner

GELATIN, CHEMICALLY MODIFIED PRODUCT THEREOF, AQUEOUS COMPOSITION AND MEDICAL LAMINATE CONTAINING SAME, PRODUCTION METHOD FOR MEDICAL LAMINATE, AND CELL SHEET ISOLATION METHOD

TECHNICAL FIELD

The present invention relates to a gelatin or a chemically modified product thereof, an aqueous composition and a medical laminate containing the same, as well as a method for producing the medical laminate and a method for isolating a cell sheet. More specifically, the present invention relates to a gelatin or a chemically modified product thereof used in an aqueous gelatin composition that is rapidly gelatinized at a temperature greater than or equal to 27° C., and undergoes dissolution from a gel state at a temperature greater than or equal to about 32° C., and an aqueous composition and a medical laminate containing the same, as well as a method for producing the medical laminate and a method for isolating a cell sheet.

BACKGROUND ART

In recent years, regenerative medicine based on a cell sheet engineering technique is paid attention, and transplantation of various kinds of cell sheets is attempted. A monolayer sheet, a laminate of sheets of the same cells, and a laminate of sheets of several kinds of cells are used as a cell sheet. For example, clinical application of a cell sheet to skin, corneas, retinas, heart disease, ears, cartilages, pancreases, livers, lungs, teeth, esophagi, and bladders is ongoing.

A cell sheet is very fragile, and is easy to wrinkle and break after isolation. Storage and transfer of a cultured cell sheet as it is can maintain the freshness of the cell sheet, but storage and transfer with little vibration of a culture solution is not easy. Therefore, a better method for storing and transferring the cell sheet is desired.

A gelatin is extracted thermally from skin, bones or the like, and contains modified collagen as a main ingredient. As a gelatin is almost equivalent to collagen chemically, it has excellent biocompatibility, and is decomposed and absorbed in vivo. A molded product such as particulates, films, capsules, and sponges can be produced from an aqueous gelatin solution, and the molded product is broadly used in the field of regenerative medicine. As the aqueous gelatin solution has properties of being gelatinized at a low temperature and being melted when heated, it has been used as a jelly in food field for a long time. However, such temperature reversible sol-gel transition has hardly ever been applied to medical technology.

Japanese Patent Laying-Open No. 2011-172925 (PTD 1) describes a medical laminate essentially consisting of a sheet-shaped cell culture, and a support layer that supports the sheet-shaped cell culture and contains a biocompatible compound capable of converting into a polymer gel at a normal temperature. In Example 1 of PTD 1, a gelatin is used as a biocompatible compound capable of converting into a polymer gel at a normal temperature, and coagulated at 4° C. to produce a laminate, and then the laminate is heated to 37° C. and the gelatin is melted to obtain a sheet-shaped cell culture. However, the gelatin used in Example 1 is an ordinary gelatin with a low melting point, and is not gelatinized at room temperature such as 25° C. Therefore, if the method described in Example 1 is used, a laminate in which cells and tissues are embedded needs to be stored and transferred while being controlled to a temperature lower than room temperature, for example, 4° C. However, since functions of the cells and the tissues are significantly declined at such a low temperature, a cell sheet obtained from the laminate is not suitable for regenerative medicine.

Journal of Bioscience and Bioengineering, 118(1), 112-115 (2014) (NPD 1) and Japanese Patent Laying-Open No. 2014-100110 (PTD 2) disclose an uncleaved gelatin (UCG) having a content of short hydrolyzed peptides decreased by thermal denaturation of pigskin collagen-derived atelocollagen at a moderate temperature of 60° C. An aqueous solution containing 5% by mass of the UCG has a melting point of 31° C. that is higher than that of an aqueous solution containing 5% by mass of an ordinary gelatin, and is gelatinized rapidly at 25° C. (FIG. 2B of NPD 1). FIG. 1B of NPD 1 shows that the aqueous solution containing 5% by mass of the UCG showed dissolution at 37° C., was gelatinized when cooled to 23° C., and quickly showed dissolution when heated to 37° C. Accordingly, if the UCG is added to a cell sheet at a culture temperature of 37° C. and gelatinized at 23° C. and a generated cell sheet is transferred and reheated to 37° C. at a destination, the cell sheet can be isolated by dissolving the UCG.

In temperature-responsive cell cultureware for cell sheet collection such as UpCell (registered trademark: CellSeed Inc.) widely used in cell sheet engineering at present, a surface of the cultureware changes its property reversibly from hydrophobic to hydrophilic at a certain temperature as a boundary. The temperature varies because different cell types have different adhesive properties, but for example, at a temperature lower than about 27° C., a cell sheet can be separated from the surface of the cultureware, and collected. Poly(N-isopropyl acrylamide) (PNIPAM) is used as the temperature-responsive cell cultureware for cell sheet collection, and there are many kinds of PNIPAMs as described in Material Matters (trademark), Vol. 5, Vo. 3, published by Aldrich, pp. 4-9 (2011.2) (NPD 2), and each of the PNIPAMs can have a different temperature for cell adhesion. When a cell sheet is prepared and transferred using the temperature-responsive cell cultureware for cell sheet collection, the following steps are practical: adding a sol-like cell sheet protective material to the cell sheet on the cultureware at a temperature such as 37° C. (a first temperature); gelatinizing the cell sheet protective material while keeping the cell sheet adhered to the cultureware at a temperature higher than 27° C. (a second temperature); cooling the cell sheet protective material to a temperature lower than 27° C. (a third temperature) to separate the cell sheet protected by the cell sheet protective material from the cultureware and transfer the cell sheet; and reheating the cell sheet to 37° C. (the first temperature) at a destination to isolate the cell sheet. A cell sheet protective material having an ability of temperature reversible sol-gel transition that can realize such steps is desired, but has not yet been developed. Since the UCG as described in NPD 1 or the like is not gelatinized rapidly at a temperature greater than or equal to 27° C., it cannot be used as the above cell sheet protective material.

Accordingly, a cell sheet protective material having an ability of temperature reversible sol-gel transition that the material is gelatinized rapidly at a temperature greater than or equal to 27° C., and undergoes dissolution from a gel state at a temperature greater than or equal to about 32° C. has been desired.

CITATION LIST

Patent Document

PTD 1: Japanese Patent Laying-Open No. 2011-172925
PTD 2: Japanese Patent Laying-Open No. 2014-100110

Non Patent Document

NPD 1: Journal of Bioscience and Bioengineering, 118 (1), 112-115 (2014)
NPD 2: Material Matters (trademark), Vol. 5, Vo. 3, published by Aldrich, pp. 4-9 (2011.2)

SUMMARY OF INVENTION

Technical Problems

An object to be achieved by the present invention is to provide an aqueous gelatin composition that is gelatinized rapidly at a temperature greater than or equal to 27° C., and undergoes dissolution from a gel state at a temperature greater than or equal to about 32° C., and a gelatin or the like used therein. Another object of the present invention is to provide a medical laminate including the aqueous gelatin composition, as well as a method for producing the medical laminate and a method for isolating a cell sheet.

Solutions to Problems

In order to achieve the above objects, the present inventors studied gelatins prepared from various kinds of raw materials by various treatment operations. As a result, they completed the present invention based on the surprising finding that an aqueous composition containing 5% by mass of a gelatin, the gelatin containing 10 to 50% by mass of a component having a higher molecular weight than a γ-chain does, and a component having a lower molecular weight than an α-chain does in such an amount that a value obtained by subtracting the low-molecular weight component content from the high-molecular weight component content is greater than or equal to 0% by mass, is gelatinized rapidly within 30 minutes at a temperature greater than or equal to 27° C., and undergoes dissolution from a gel state at a temperature greater than or equal to about 32° C. The present invention includes the following items.

[1] A gelatin or a chemically modified product thereof, containing 10 to 50% by mass of a high-molecular weight component, and a low-molecular weight component in such an amount that a value obtained by subtracting a low-molecular weight component content from a high-molecular weight component content is greater than or equal to 0% by mass.

[2] The gelatin or the chemically modified product thereof according to [1], which is derived from tendon-derived collagen.

[3] A method for producing the gelatin or the chemically modified product thereof according to [1], including:
  adding collagen to water to give a solution having a collagen concentration of 0.1 to 10% by mass;
  adjusting pH of the solution to 2 to 9; and
  thermally denaturing the collagen at a temperature in a range of 40 to 80° C.

[4] The method according to [3], wherein the collagen is derived from a tendon.

[5] An aqueous composition, containing the gelatin or the chemically modified product thereof according to [1] or [2] in an amount of 0.5 to 10% by mass.

[6] A medical laminate, including a cell sheet, and one or two support layers containing the gelatin or the chemically modified product thereof according to [1] or [2] adhering to one or both surfaces of the cell sheet.

[7] A method for producing a medical laminate, including:
  coating a cell sheet formed on a culture substrate with a liquid or sol-like aqueous composition containing the gelatin or the chemically modified product thereof according to [1] or [2]; and
  gelatinizing the liquid or sol-like aqueous composition to form a support layer.

[8] A method for isolating a cell sheet, including:
  producing the medical laminate according to [6] by the method according to [7]; and
  removing the support layer.

Advantageous Effects of Invention

An aqueous gelatin composition prepared by mixing the gelatin or the like of the present invention with water is gelatinized rapidly within 30 minutes at a temperature greater than or equal to 27° C., and undergoes dissolution from a gel state at a temperature greater than or equal to about 32° C. The aqueous gelatin composition can be used to add a sol-like aqueous gelatin composition to a cell sheet on temperature-responsive cell cultureware for cell sheet collection at a temperature such as 37° C. (a first temperature), gelatinize the aqueous gelatin composition while keeping the cell sheet adhered to the cultureware at a temperature higher than 27° C. (a second temperature), then cool the aqueous gelatin composition to a temperature lower than 27° C. (a third temperature) to separate the cell sheet protected by the aqueous gelatin composition from the cultureware and transfer the cell sheet, and reheat the cell sheet to 37° C. (the first temperature) at a destination to isolate the cell sheet. The third temperature may be room temperature of about 25° C., and the cell sheet can be stored and transferred stably without damage at the temperature.

DESCRIPTION OF EMBODIMENTS

The present invention is described in detail in the following.

1. Gelatin or chemically modified product thereof

Collagen consists of three peptide chains called α-chains forming a helical structure. An ordinary gelatin obtained by treatment such as thermal decomposition of collagen is generally a mixed composition of the following components.

[Chemical 1]

high-molecular weigh component    γ-chain    β-chain    α-chain    low-molecular weight component An "α-chain" is one peptide chain, a "β-chain" has a structure in which two α-chains bond each other, and a "γ-chain" has a structure in which three α-chains bond each other. Additionally, there are a "low-molecular weight component" that is a short peptide generated by hydrolyzing an α-chain and has a lower molecular weight than that of an α-chain, and a "high-molecular weight component" that has a structure in which greater than or equal to 4 α-chains bond each other, and has a higher molecular weight than that of a γ-chain. A commercially available gelatin contains a large amount of a low-molecular weight component generated by advanced hydrolysis in its preparation process.

The gelatin of the present invention contains 10 to 50% by mass of a high-molecular weight component, and a low-molecular weight component in such an amount that a value obtained by subtracting a low-molecular weight component content from a high-molecular weight component content is greater than or equal to 0% by mass. In the gelatin of the present invention, the high-molecular weight component content may be 10 to 50% by mass, preferably 11 to 40% by mass, more preferably 12 to 35% by mass, still more preferably 13 to 30% by mass, and particularly preferably 15 to 25% by mass. When the high-molecular weight component content is greater than 50% by mass, a sol in an aqueous composition containing 1 to 10% by mass of the gelatin is extremely viscous and is not gelatinized. When the high-molecular weight component content is less than 10% by mass, the aqueous composition containing 1 to 10% by mass of the gelatin is not gelatinized rapidly at a temperature greater than or equal to 27° C.

In the gelatin of the present invention, the value obtained by subtracting the low-molecular weight component content from the high-molecular weight component content may be greater than or equal to 0% by mass, preferably greater than or equal to 2% by mass, more preferably greater than or equal to 3% by mass, still more preferably greater than or equal to 5% by mass, and particularly preferably greater than or equal to 8% by mass. When the value is less than 0% by mass, the aqueous composition containing 1 to 10% by mass of the gelatin is not gelatinized rapidly at a temperature greater than or equal to 27° C.

Contents of the α-chain, β-chain, and γ-chain are not particularly limited. The α-chain content may be 10 to 50% by mass, preferably 15 to 40% by mass, and more preferably 20 to 35% by mass. The β-chain content may be 10 to 50% by mass, preferably 15 to 40% by mass, and more preferably 20 to 35% by mass. The γ-chain content may be 10 to 50% by mass, preferably 15 to 40% by mass, and more preferably 20 to 35% by mass.

In addition, the content rate of hydroxyproline in an amino acid contained in the gelatin of the present invention is preferably greater than or equal to 10%. When the content of hydroxyproline is lowered, the temperature at which the aqueous gelatin composition is gelatinized rapidly is decreased.

Examples of the chemically modified product of the gelatin of the present invention include a chemically modified product in which a carboxyl group or an amino group in the gelatin of the present invention is chemically modified, and a chemically modified product in which proline in the gelatin of the present invention is hydroxylated. Examples of chemical modification of the carboxyl group include amidation with ammonia, amine, or glycine methyl ester. Examples of chemical modification of the amino group include succinylation, phthalation, fumarylation, and acetylation. The proline in the gelatin can be hydroxylated, for example, by acting prolyl 4-hydroxylase on the gelatin. Among the functional groups used in such chemical modification, the amino group and the carboxyl group face outside of a collagen helix, and thus a gelatinization phenomenon of the gelatin that is a partial restoration phenomenon of the collagen helix is less inhibited by the modification with the functional groups. As a result, it is possible to change various other kinds of physical properties of the gelatin without impairing an effect of the present invention of a high gelatinization temperature. Meanwhile, the hydroxylation of proline contributes to hydrogen bonding within a collagen helix, and stabilizes gelatinization of the gelatin. A preferable chemically modified product is a succinylated product in which an introduced side chain is an in-vivo metabolite, and which has an enhanced solubility in water at neutrality. The degree of chemical modification is preferably adjusted appropriately so that the chemically modified product of the gelatin can have desired physical properties. Succinylation modification of up to 80% of amino groups in the gelatin hardly changes the temperature at which an aqueous gelatin composition is gelatinized rapidly, and can increase solubility. A more preferable succinylation rate of amino groups may be 40 to 70% of the amino groups. The chemical modification can be performed according to a routine method.

2. Method for Producing Gelatin

Examples of raw materials of the gelatin of the present invention include collagen derived from animals such as cattle, pigs, chickens, ostriches, and fish, preferably cattle, pigs, chickens, and ostriches, and more preferably pigs. Examples of body parts of the animals from which collagen is collected include skin, bone, cartilages, tendons, and scales. A tendon is preferable because it has a large amount of a high-molecular weight component.

The gelatin of the present invention containing a large amount of a high-molecular weight associate and having an increased temperature of quick gelatinization is obtained by preparing extracted collagen through thermal decomposition. Examples of the extracted collagen used as a raw material can include atelocollagen, acid-extracted collagen, and alkali-treated collagen. Atelocollagen is preferable. Atelocollagen is prepared by adding a protease such as pepsin, chymosin, cathepsin D, or renin, and digesting a telopeptide present at an N-terminus or a C-terminus, and it has low viscosity and is easy to handle, because the telopeptide has been removed. Tendon-derived atelocollagen is more preferable.

To the extracted collagen, water is added to give an aqueous solution having a collagen concentration of 0.1 to 10% by mass, and pH of the aqueous solution is adjusted to a specific pH. The collagen concentration is preferably 0.15 to 5% by mass, and more preferably 0.2 to 3% by mass. The pH may be 2 to 9, preferably 3 to 8, and more preferably 4 to 7. Then, the aqueous solution is thermally denatured by retaining at a temperature in the range of 40° C. to 80° C. for 5 minutes to 24 hours. The thermal denaturation temperature is preferably a temperature in the range of 45° C. to 70° C., and more preferably a temperature in the range of 50° C. to 60° C. Preferably, the thermal denaturation time is made long if the thermal denaturation temperature is low, and is made short if the temperature is high. The thermal denaturation time may be a time in the range of 15 minutes to 15 hours. By the thermal denaturation, the collagen helical structure is broken, and a mixture of a high-molecular weight component, a γ-chain, a β-chain, an α-chain, and a low-molecular weight component is obtained.

The gelatin of the present invention is obtained by drying the thermally denatured aqueous gelatin solution. Drying can be performed according to a routine method, and examples of the drying method include ventilation drying, spray drying, and lyophilization. In addition, the obtained gelatin may be chemically modified by a routine method to provide the chemically modified product thereof.

A gelatin mixture satisfying the conditions of the present invention can be produced by mixing a plurality of gelatins, high-molecular weight components, γ-chains, β-chains, α-chains, or low-molecular weight components appropriately.

3. Aqueous Composition

An aqueous composition exhibiting temperature reversible sol-gel transition can be obtained by mixing the gelatin or the chemically modified product thereof of the present invention with water to give a mixture having a gelatin concentration of 0.5 to 10% by mass. The gelatin concentration of the aqueous composition of the present invention can be changed according to the purpose of use. If the aqueous composition is used in a medical laminate, the gelatin concentration is preferably 1 to 8% by mass, more preferably 2 to 7% by mass, and still more preferably 3 to 6% by mass.

Water used can be selected appropriately according to the purpose of use. If the water is used in a medical laminate, preferably sterile water, for example, saline can be used. Optionally, additives such as buffers including Tris buffers, HEPES buffers, phosphate buffers, and citrate buffers, preservatives, and bactericides can be added.

The aqueous composition of the present invention is gelatinized rapidly at a temperature greater than or equal to 27° C., and undergoes dissolution from a gel state at a temperature greater than or equal to about 32° C. The present inventors define a "practical maximum gelatinization temperature (Tg-max)" as a temperature of rapid gelatinization, and use the temperature herein. When temperature-responsive cell cultureware for cell sheet collection such as UpCell (registered trademark: CellSeed Inc.) is used at 27° C., a cell sheet can be separated in about 30 minutes. Therefore, the Tg-max is the maximum temperature to give a hardness greater than or equal to a practical hardness (G'=50 Pa) to the aqueous composition within 30 minutes. A method for measuring the Tg-max is described below. In addition, a "minimum melting temperature" is used as a temperature at which a gel is dissolved. Accordingly, the aqueous composition of the present invention has a Tg-max greater than or equal to 27° C. and a minimum melting temperature greater than or equal to 32° C.

The Tg-max and the minimum melting temperature of the aqueous composition of the present invention can be adjusted to desired values by adjusting the high-molecular weight component content and the low-molecular weight component content in the gelatin of the present invention as described in Example 15, or adjusting the concentration of the gelatin or the like of the present invention as described in Example 16, according to the purpose of use of the aqueous composition of the present invention.

4. Medical Laminate

The medical laminate of the present invention includes a cell sheet, and one or two support layers containing the gelatin or the chemically modified product thereof of the present invention adhering to one or both surfaces of the cell sheet. The aqueous composition described in the above section 3. is used as the one or two support layers containing the gelatin or the chemically modified product thereof of the present invention adhering to one or both surfaces of the cell sheet.

The cell sheet is a sheet-shaped material in which cells are linked to one another, and is typically composed of one cell layer, but may also be a cell sheet composed of greater than or equal to 2 cell layers. The cells may be linked to one another directly or via a mediator. The mediator is not limited as long as it can link the cells at least mechanically, and examples of the mediator include an extracellular matrix. The mediator is preferably derived from cells, and particularly is derived from cells that form a cell culture. The cells are linked at least mechanically, and furthermore, they may be linked functionally, for example, chemically and electrically. The cells of the cell sheet may be any cells, and examples of the cells include myoblast cells, myocardial cells, fibroblast cells, synovial cells, corneal epithelial cells, oral mucosa epithelial cells, endothelial cells, hepatic cells, pancreatic cells, periodontal ligament cells, and cutaneous cells. Examples of animal species of the cells include human, non-human primates, dog, cat, pig, horse, goat, sheep, mouse, and rat.

The content of the gelatin or the chemically modified product thereof of the present invention that is used as a support layer in the aqueous composition described in the above section 3. may be 1 to 10% by mass, preferably 2 to 8% by mass, more preferably 3 to 7% by mass, and still more preferably 4 to 6% by mass.

The support layer preferably adheres to the whole of the cell sheet, but may adhere to a part of the cell sheet. The thickness of the support layer is not limited as long as the support layer can support the cell sheet, and the thickness may be 1 to 10 mm, preferably 2 to 7 mm, more preferably 3 to 5 mm from the point of view of strength of the support layer to avoid breakage of the cell sheet during the course of separation.

In the present invention, since the support layer adheres to one or both surfaces of the cell sheet, and has strength, it can support the fragile cell sheet securely. Accordingly, the support layer can not only facilitate stable storage and transfer of the cell sheet, but also facilitate separation of the cell sheet from a culture substrate.

Even if the medical laminate of the present invention is stored for about 7 days at room temperature, there are very few dead cells in the cell sheet as shown in Example 19.

Since the number of dead cells is small, the medical laminate can be stored and transferred at room temperature, not at a low temperature at which functions of cells and tissues are significantly declined.

5. Method for Producing Medical Laminate and Method for Isolating Cell Sheet

The medical laminate of the present invention can be produced by a method including: coating a cell sheet formed on a culture substrate with a liquid or sol-like aqueous composition containing the gelatin or the chemically modified product thereof of the present invention; and gelatinizing the liquid or sol-like aqueous composition to form a support layer. In addition, a medical laminate having support layers on both the surfaces of a cell sheet can be produced by a method including: coating a cell sheet formed on a culture substrate with a liquid or sol-like aqueous composition containing the gelatin or the chemically modified product thereof of the present invention; gelatinizing the liquid or sol-like aqueous composition to form a first support layer; then separating the cell sheet together with the gelatinized support layer from the culture substrate; coating a surface of the cell sheet having been in contact with the culture substrate with a liquid or sol-like aqueous composition containing the gelatin or the chemically modified product thereof of the present invention; and gelatinizing the liquid or sol-like aqueous composition to form a second support layer.

A cell sheet is generally formed on a culture substrate. The culture substrate is not particularly limited, as long as the cell sheet can be formed thereon. A surface of the culture substrate may be coated with a material having physical properties that change in response to stimuli such as temperature and light. It is possible to change the physical properties of the material such as hydrophilicity or hydrophobicity and promote separation of a cell culture attached to the material by giving a predetermined stimulus to the material. Temperature-responsive cell cultureware for cell sheet collection such as UpCell (registered trademark: manufactured by CellSeed Inc.) can be used as the culture substrate.

The temperature-responsive cell cultureware for cell sheet collection can be used to add a sol-like aqueous composition of the present invention to a cell sheet on the cultureware at a temperature such as 37° C. (a first temperature), gelatinize the aqueous composition of the present invention while keeping the cell sheet adhered to the cultureware at a temperature greater than or equal to 27° C. (a second temperature), then cool the aqueous composition to a temperature lower than 27° C. (a third temperature) to separate the cell sheet protected by the aqueous composition of the present invention from the cultureware and transfer the cell sheet, and reheat the cell sheet to a temperature such as 37° C. (the first temperature) to isolate the cell sheet.

The case where the temperature-responsive cell cultureware for cell sheet collection will be described more specifically.

First, the sol-like aqueous composition of the present invention is added to the cell sheet on the temperature-responsive cell cultureware for cell sheet collection at the first temperature. The content of the gelatin or the chemically modified product thereof of the present invention in the aqueous composition of the present invention may be 1 to 10% by mass, preferably 2 to 8% by mass, more preferably 3 to 7% by mass, and still more preferably 4 to 6% by mass. The amount of the liquid or sol-like aqueous composition according to the above section 3. may be an amount required to provide enough thickness to support the cell sheet, for example, an amount required to provide a thickness of 1 to 10 mm, preferably an amount required to provide a thickness of 2 to 7 mm, and more preferably an amount required to provide a thickness of 3 to 5 mm. The first temperature may be a temperature in the range of 34° C. to 38° C., and preferably 37° C.

Next, the aqueous composition of the present invention is gelatinized while the cell sheet is kept adhered to the cultureware at a temperature greater than or equal to 27° C. (a second temperature). The second temperature may be a temperature in the range of 27° C. to 32° C., preferably a temperature in the range of 28° C. to 31° C., more preferably a temperature in the range of 28° C. to 30° C. The solidification or gelatinization time may be 10 minutes to 1 hour, and preferably 15 to 30 minutes.

Then, the aqueous composition is cooled to a temperature lower than 27° C. (a third temperature), and a cell sheet protected by the aqueous composition of the present invention is separated from the cultureware. The third temperature may be a temperature in the range of 20° C. to 25° C.

The obtained medical laminate having the aqueous composition of the present invention on one surface can be turned over using tweezers or the like, and a second aqueous composition of the present invention can be formed on a surface of the cell sheet having been in contact with the culture substrate in the same manner as described above to produce a medical laminate having the aqueous composition of the present invention on both surfaces.

The obtained cell sheet protected by the aqueous composition of the present invention is reheated to a temperature such as 37° C. (the first temperature) to isolate the cell sheet. The first temperature is as mentioned above.

After removing the aqueous composition of the present invention, the cell sheet may be washed with water as necessary, but even if a small amount of the gelatin remains and is attached to the cell sheet, the gelatin has no problem in medical use because of its biocompatibility. In addition, the medical laminate can be directly applied to a living body without removal of the aqueous composition of the present invention. When the medical laminate is directly applied to a living body, since the aqueous composition of the present invention is dissolved by body temperature of the living body, or is decomposed by enzymes in the living body, the aqueous composition may be retained in the living body, or may be removed during medical practice. Direct application of the medical laminate to the living body eliminates the necessity of using a device for transplantation to apply a cell sheet.

6. Other Uses of Gelatin

The gelatin of the present invention can be applied to various uses such as culture media, food, cosmetics, and medicine in addition to the cell sheet based on its properties.

The aqueous composition of the present invention can have a minimum melting temperature greater than or equal to 37° C. by increasing the concentration of the gelatin or the like of the present invention. In this case, since the aqueous composition does not melt at 37° C., cells can be dispersed in the aqueous composition of the present invention in a gel state, and can be cultured at 37° C. as they are. Since the aqueous composition of the present invention maintains the gel state at 37° C., the aqueous composition of the present invention in a gel state that contains the cells can be transplanted to a living body as it is. In this case, the gelatin or the like of the present invention is decomposed slowly by enzymes in the living body.

Examples of the food include instant food, vegetables, fruits, fibrous food that activates digestion, and functional food. Examples of cosmetics and medicine include percutaneous formulations, internal agents, suppositories, and transvaginal agents.

EXAMPLES

The present invention is described in detail below by way of examples, comparative examples, and evaluation tests, however, they should not be understood to limit the present invention.

Evaluation tests of aqueous gelatin compositions prepared in examples and comparative examples were performed according to the following methods.

(a) Analysis of Gelatin Component Content

Contents of a high-molecular weight component, a γ-chain, a β-chain, an α-chain, and a low-molecular weight component in a gelatin were analyzed by polyacrylamide electrophoresis (SDS-PAGE) and its densitogram.

Mini-PROTEAN TGX precast gel (registered trademark: manufactured by Bio-Rad Laboratories, Inc.) was used as gel for electrophoresis. Gelatins of examples and comparative examples were mixed with sodium dodecyl sulfate (SDS: manufactured by Wako Pure Chemical Industries, Ltd.), bromphenol blue (BPB: manufactured by Wako Pure Chemical Industries, Ltd.), glycerin (manufactured by KANTO CHEMICAL CO., INC.), and a Tris buffer (manufactured by Wako Pure Chemical Industries, Ltd.), and the mixture was prepared to have a sample concentration of 10 μg/lane, and heated at 100° C. for 3 minutes. To each well, 10 μL of the sample solution was applied, and electrophoresis was performed according to a predetermined method described in a protocol. Precision Plus Protein Blue standards (trademark: manufactured by Bio-Rad Laboratories, Inc.) was used as a molecular weight marker. In addition, since pig tendon-derived atelocollagen is found to be composed of α1, α2, β11, β12, γ, and a high-molecular weight component by SDS-PAGE, it was used as a control for peaks of the components. After electrophoresis, the sample solution was dyed with Coomassie Brilliant Blue (CBB: manufactured by Wako Pure Chemical Industries, Ltd.). Furthermore, the dyed sample solution was decolored using a decoloring liquid prepared with methanol (manufactured by Wako Pure Chemical Industries, Ltd.), acetic acid (manufactured by Wako Pure Chemical Industries, Ltd.), and ultrapure water.

A densitogram used for analyzing contents of a high-molecular weight component, a γ-chain, a β-chain, an α-chain, and a low-molecular weight component contained in a gelatin was generated using image analysis software, ImageJ (NIH). The method is as follows. Decolored gels were dried with a gel dryer (manufactured by Bio-Rad Laboratories, Inc.) and an electronic image of the obtained dried product was obtained using a scanner. Using image processing by ImageJ, a background was subtracted, and the position of each band and luminance calculated from the number of pixels were formed into a graph per lane corresponding to the band width in electrophoresis to generate a densitogram. Based on the gel image, a baseline was drawn on the densitogram, and each peak area was calculated to quantify the concentration of each peak. Composition ratios of a high-molecular weight component, a γ-chain, a β-chain, an α-chain, and a low-molecular weight component contained in the gelatin were calculated from the area ratio of each band to the total area of the whole lanes.

Further, as for the band of a low-molecular weight component, all components having a molecular weight lower than 100 kDa of the molecular weight marker were selected. As for the band of an α-chain, a peak in the range of 100 kDa to 150 kDa of the molecular weight marker on the densitogram was selected. As for the band of a β-chain, a peak corresponding to β11 and β12 on the densitogram was selected. As for the band of a γ-chain, around a peak corresponding to the γ-chain on the densitogram, components including a component having a molecular weight lower than that of a component at the deepest valley located between the γ-chain and a high-molecular weight component were selected. As for the band of a high-molecular weight component, a component having a molecular weight higher than that of a component at the deepest valley located between the γ-chain and the high-molecular weight component on the densitogram was selected.

REFERENCE LITERATURE

Rasband, W. S., ImageJ, U. S. National Institutes of Health, Bethesda, Md., USA, http://imagej.nih.gov/ij/, 1997-2012.

Schneider, C. A., Rasband, W. S., Eliceiri, K. W. "NIH Image to ImageJ: 25 years of image analysis". Nature Methods 9, 671-675, 2012.

(b) Measurement of Tg-Max

The Tg-max was measured by using a dynamic viscoelasticity measuring device (manufactured by Thermo Fisher Scientific K.K., type: MARSIII). Using phosphate buffered saline (PBS: manufactured by Sigma-Aldrich) as a solvent, an aqueous gelatin composition containing 5.0% by mass of a gelatin was prepared from gelatins of examples and comparative examples, and used as a sample. In a double-cone sensor (60 mm in internal diameter, cone angle 1°) heated to 37° C., 3.0 ml of the aqueous gelatin composition heated to 50° C. was filled, and cooled to a target temperature at −1.2° C./min to trace changes of the storage elastic modulus G'. Time until the G' reaches 50 Pa was measured by changing the target temperature to at least 3 points. A relation between the storage elastic modulus G' (Pa) indicated on the vertical axis and time (min) indicated on the horizontal axis was plotted, and a primary approximate expression was calculated by a least-squares method. The temperature at which the G' reaches 50 Pa in 30 minutes was calculated as the Tg-max from the approximate expression. It should be noted that the dynamic viscoelasticity measurement to measure G' was performed at a frequency of 1 Hz under strain control at a shear strain of 0.01.

(c) Measurement of minimum melting temperature

The minimum melting temperature was measured by using the same dynamic viscoelasticity measuring device as in (b). An aqueous gelatin composition prepared in the same manner as in (b) was heated to 50° C., and 3.0 ml of the aqueous gelatin composition was filled in a double-cone sensor heated to 37° C. Then, gelatinization and melting of the gelatin were traced by dynamic viscoelasticity measurement under strain control by using the following measuring profiles.

(i) Temperature: a change from 37° C. to 4° C. at −3° C./min; shear strain: 0.005; frequency: 1 Hz.

(ii) Temperature: 4° C. (120 min); shear strain: 0.001; frequency: 1 Hz.

(iii) Temperature: a change from 4° C. to x° C. (+1.2° C./min); shear strain: 0.01; frequency: 1 Hz.

(iv) Temperature: x° C. (30 min); shear strain: 0.005; frequency: 1 Hz.

(v) Temperature: a change from x° C. to x+1° C. (+1.2° C./min); shear strain: 0.005; frequency: 1 Hz.

(vi) Profiles (iv) and (v) are repeated in such a manner that the temperature increases gradually by +1° C.

Such a gradual temperature increase was performed until G' under a fixed temperature reached less than 1 Pa, and the temperature when G' reached less than 1 Pa was regarded as the minimum melting temperature.

(d) Evaluation of Cell Viability of Cells Isolated from Medical Laminate Using Hemocytometer In order to evaluate cell viability quantitatively, a hemocytometer was used to count the number of living cells and dead cells. An aqueous gelatin composition of each of the examples was mixed with a buffer (Hanks' Balanced Salt Solution: manufactured by Life Technologies) so that the mixture would have a substrate concentration to 5% by mass, and the mixture was kept warm at 37° C. to prepare a sol substrate. Meanwhile, human neonatal skin fibroblast cells NB1RGB (provided by RIKEN BioResource Center, Resource No. RBRC-RCB0222) were seeded on a temperature-responsive cell cultureware (UpCell (registered trademark): manufactured by CellSeed Inc.), and the cells were rendered overconfluent to make a cell sheet. The cell sheet was left to stand on a thermo plate kept warm at 37° C., and then was washed with a buffer kept warm at 37° C. After covering the surface of the cell sheet with the sol-like aqueous gelatin composition, the thermo plate was cooled to 27° C. for 30 minutes to gelatinize the sol substrate. The gel-like aqueous gelatin solution was separated together with the cell sheet from the cultureware, and transferred to a floating cell culture plate with the surface of the cell sheet facing upward. The surface of the cell sheet was covered with the sol-like aqueous gelatin solution kept warm at 37° C. to obtain a medical laminate. Assuming domestic transportation of the medical laminate to another place and preservation until the medical laminate is applied to surgery, the medical laminate was left to stand at room temperature for a week.

After the medical laminate was left to stand at room temperature for a week, a buffer containing 1% collagenase (manufactured by Wako Pure Chemical Industries, Ltd.)/0.2% trypsin inhibitor (manufactured by Wako Pure Chemical Industries, Ltd.) was added in an amount equivalent to the amount of the medical laminate, the mixture was transferred to a $CO_2$ incubator (5% $CO_2$, 37° C.), and shaken for 30 minutes to dissolve the aqueous gelatin composition. In order to isolate cells, the mixture was centrifuged with a centrifugal separator (himacCR-GIII: manufactured by Hitachi Koki Co., Ltd.) at 1000 rpm for 3 minutes and the supernatant was removed. After repeating steps of adding a buffer, centrifuging the mixture, and removing the supernatant twice, sample cells were collected. A cell mass was dispersed in a buffer to prepare a cell suspension, and 100 μl of the suspension was collected and dyed with 0.4% trypan blue. To a hemocytometer equipped with a cover glass (improved Neubauer: manufactured by Sunlead Glass Corp.), 10 μl of the dyed cells were dropped, and the number of dead cells dyed with trypan blue and the number of living cells that were not dyed with trypan blue were counted. A higher cell viability is more preferable, and the cell viability greater than or equal to 90% is preferable.

{Cell viability (%)}={1−(number of dead cells)/
(number of living cells+number of dead cells)
}×100

Example 1

<Preparation of Gelatin>

An aqueous solution at pH 3.0 containing 0.3% by mass of pig tendon-derived atelocollagen was prepared, and heat treated at 60° C. for 0.25 hours. Then, pH of the aqueous solution was adjusted to 7.0 with a 1 N aqueous sodium hydroxide solution, and the solution was lyophilized to obtain a gelatin of Example 1.

Examples 2 to 14 and Comparative Examples 1 to 7

<Preparation of Gelatin>

Gelatins of Examples 2 to 14 and Comparative Examples 1 to 5 were prepared in the same manner as in the preparation of Example 1, except that the raw materials and treatment time or treatment temperature were changed as shown in Table 1.

Raw materials used in Comparative Examples 4 and 5 are both commercially available collagen, Collagen BM (pig-skin-derived collagen: manufactured by Nitta Gelatin Inc.). Raw materials used in Comparative Examples 6 and 7 are both commercially available. In Comparative Example 6, beMatrix gelatin LS-H (pigskin-derived collagen: manufactured by Nitta Gelatin Inc.) is used, and in Comparative Example 7, a widely used gelatin (pigskin-derived collagen: manufactured by Nitta Gelatin Inc.) was used.

TABLE 1

| No. | Raw material | Treatment pH | Treatment temperature (° C.) | Treatment time (hour) |
| --- | --- | --- | --- | --- |
| Example 1 | Pig-tendon collagen | 3.0 | 60 | 0.25 |
| Example 2 | Pig-tendon collagen | 3.0 | 60 | 1.0 |
| Example 3 | Pig-tendon collagen | 3.0 | 60 | 2.0 |
| Comparative Example 1 | Pig-tendon collagen | 3.0 | 60 | 5.0 |
| Example 4 | Pig-tendon collagen | 7.0 | 60 | 1.0 |
| Example 5 | Pig-tendon collagen | 7.0 | 60 | 5.0 |
| Example 6 | Pig-tendon collagen | 7.0 | 60 | 15.0 |
| Example 7 | Pig-tendon collagen | 3.0 | 70 | 0.25 |
| Comparative Example 2 | Pig-tendon collagen | 3.0 | 70 | 2.0 |
| Example 8 | Pig-tendon collagen | 7.0 | 70 | 1.0 |
| Example 9 | Pig-tendon collagen | 7.0 | 70 | 5.0 |
| Comparative Example 3 | Pig-tendon collagen | 7.0 | 70 | 15.0 |
| Example 10 | Pig-tendon collagen | 3.0 | 50 | 0.25 |
| Example 11 | Pig-tendon collagen | 3.0 | 50 | 1.0 |

TABLE 1-continued

| No. | Raw material | Treatment pH | Treatment temperature (° C.) | Treatment time (hour) |
|---|---|---|---|---|
| Example 12 | Pig-tendon collagen | 3.0 | 50 | 2.0 |
| Example 13 | Pig-tendon collagen | 3.0 | 50 | 5.0 |
| Comparative Example 4 | Collagen BM (pigskin collagen) | 3.0 | 60 | 1.0 |
| Comparative Example 5 | Collagen BM (pigskin collagen) | 7.0 | 60 | 1.0 |
| Example 14 | Ostrich skin collagen | 3.0 | 60 | 1.0 |
| Comparative Example 6 | beMatrix gelatin LS-H (pigskin) | — | — | — |
| Comparative Example 7 | Widely used gelatin (pigskin) | — | — | — |

<Evaluation Test 1>
<Composition, Tg-Max, and Minimum Melting Temperature of Gelatins of Examples 1 to 14 and Comparative Examples 1 to 7>

Compositions of gelatins of Examples 1 to 14 and Comparative Examples 1 to 7 were analyzed. Table 2 shows the analysis results. Further, each of the gelatins was dissolved in phosphate buffered saline to give an aqueous composition containing 5% by mass of the gelatin, and the Tg-max and minimum melting temperature of the aqueous composition were measured. Table 2 shows the results.

TABLE 2

| No. | High-molecular weight component | γ | β | α | Low-molecular weight component | Tg-max | Minimum melting temperature | Minimum melting temperature (estimated) |
|---|---|---|---|---|---|---|---|---|
| Example 1 | 18.4 | 25.5 | 27.8 | 23.8 | 4.4 | 29.8 | — | 34.8 |
| Example 2 | 13.9 | 30.7 | 28.6 | 24.6 | 2.1 | 28.3 | 33.8 | — |
| Example 3 | 11.1 | 33.4 | 30.9 | 20.9 | 3.7 | 28.6 | — | 33.3 |
| Comparative Example 1 | 6.8 | 27.5 | 25.3 | 26.9 | 13.5 | 26.3 | — | 31.3 |
| Example 4 | 16.0 | 25.7 | 24.4 | 30.3 | 3.6 | 30.8 | 35.4 | — |
| Example 5 | 12.8 | 27.5 | 26.5 | 26.6 | 6.5 | 29.0 | — | 34.0 |
| Example 6 | 10.5 | 32.7 | 24.4 | 24.3 | 8.1 | 27.3 | — | 32.3 |
| Example 7 | 10.2 | 34.6 | 27.3 | 26.4 | 1.6 | 29.3 | — | 34.3 |
| Comparative Example 2 | 9.1 | 36.1 | 21.7 | 20.8 | 12.2 | 25.4 | — | 30.4 |
| Example 8 | 12.7 | 30.4 | 24.2 | 29.0 | 3.8 | 29.1 | — | 34.1 |
| Example 9 | 11.0 | 31.8 | 26.6 | 23.2 | 7.4 | 27.4 | — | 32.4 |
| Comparative Example 3 | 2.1 | 30.1 | 31.1 | 27.6 | 9.2 | 24.6 | — | 29.6 |
| Example 10 | 20.7 | 24.7 | 25.3 | 26.1 | 3.2 | 30.0 | — | 35.0 |
| Example 11 | 21.3 | 23.3 | 28.0 | 23.9 | 3.5 | 30.0 | — | 35.0 |
| Example 12 | 18.0 | 21.5 | 27.3 | 24.2 | 9.1 | 29.1 | — | 34.1 |
| Example 13 | 15.8 | 25.8 | 23.1 | 25.6 | 9.6 | 28.7 | — | 33.7 |
| Comparative Example 4 | 8.3 | 27.8 | 21.5 | 35.8 | 6.7 | 26.4 | — | 31.4 |
| Comparative Example 5 | 4.9 | 12.0 | 21.8 | 48.7 | 12.6 | 25.3 | — | 30.3 |
| Example 14 | 34.0 | 21.7 | 16.4 | 23.0 | 5.0 | 28.4 | 33.8 | — |
| Comparative Example 6 | 4.7 | 29.2 | 22.0 | 37.5 | 6.6 | 23.8 | — | 28.8 |
| Comparative Example 7 | 6.0 | 26.6 | 53.4 | 0.1 | 14.0 | 24.0 | — | 29.0 |

Figure 1:
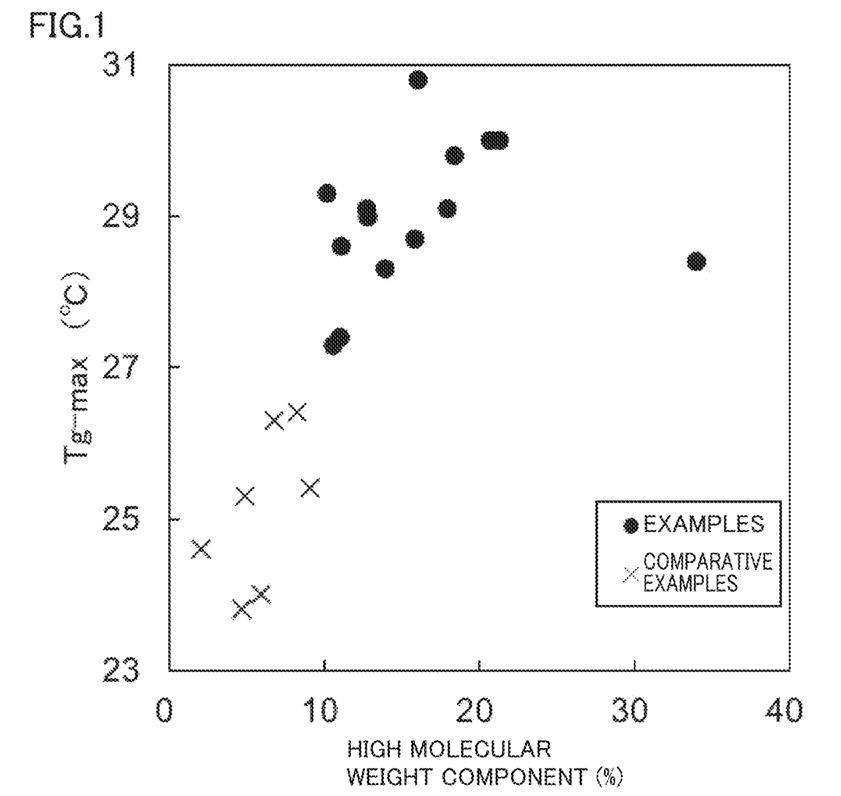
FIG. 1 shows a relation between the high-molecular weight component content and the Tg-max in gelatins of Examples 1 to 14 and Comparative Examples 1 to 7.
Figure 2:
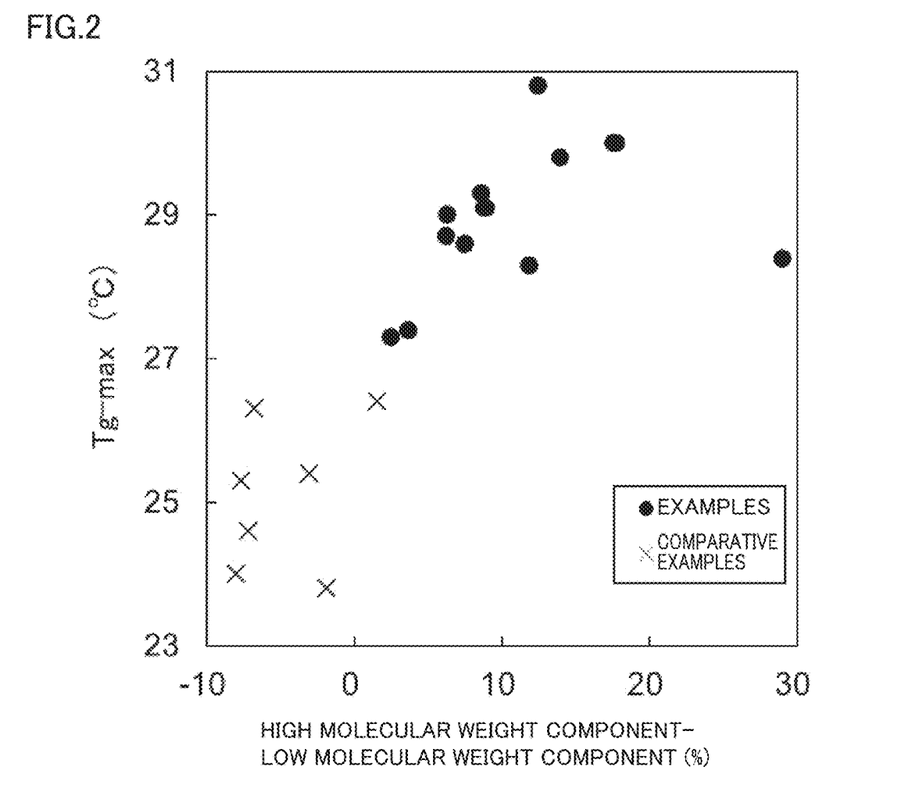
FIG. 2 shows a relation between a value obtained by subtracting the low-molecular weight component content from the high-molecular weight component content and the Tg-max in gelatins of Examples 1 to 14 and Comparative Examples 1 to 7.

FIG. 1 shows a relation between the high-molecular weight component content and the Tg-max in gelatins of Examples 1 to 14 and Comparative Examples 1 to 7. Further, FIG. 2 shows a relation between a value obtained by subtracting the low-molecular weight component content from the high-molecular weight component content and the Tg-max in gelatins of Examples 1 to 14 and Comparative Examples 1 to 7. FIG. 1 shows that in a gelatin containing 10 to 50% by mass of a high-molecular weight component, an aqueous composition containing the gelatin in an amount of 5% by mass has a Tg-max greater than equal to 27° C., and is gelatinized rapidly at the temperature. Further, from FIG. 2, it is found that in a gelatin containing a high-molecular weight component and a low-molecular weight component in such an amount of that a value obtained by subtracting the low-molecular weight component content from the high-molecular weight component content is greater than or equal to 0% by mass, an aqueous composition containing the gelatin in an amount of 5% by mass has a Tg-max greater than or equal to 27° C., and is gelatinized rapidly at the temperature.

As shown in Table 2, the difference between the Tg-max and the minimum melting temperature of aqueous compositions containing 5% by mass of gelatins of Example 2, 4, and 14 is appropriately 5° C. Therefore, although the minimum melting temperatures of gelatins other than these gelatins are not measured, a value obtained by adding 5° C.

to the Tg-max is determined as an estimated value of the minimum melting temperature, and shown in Table 2.

Example 15

<Mixing Experiment of Gelatin>

The gelatin of Example 4 and the gelatin of Comparative Example 7 were mixed at a weight ratio of 1:1, and the Tg-max of an aqueous composition containing 5% by mass of the resultant gelatin was measured. As a result, the Tg-max was 27.3° C. Since an aqueous solution containing 5% by mass of the gelatin of Example 4 had a Tg-max of 30.8° C. and an aqueous solution containing 5% by mass of the gelatin of Comparative Example 7 had a Tg-max of 24.0° C., the Tg-max of 27.3° C. was almost equal to the mean value between the two Tg-max values.

Accordingly, it was found that if the high-molecular weight component content, and a value obtained by subtracting the low-molecular weight component content from the high-molecular component content are adjusted by mixing a plurality of different kinds of gelatins or a plurality of gelatin components, a gelatin having a Tg-max corresponding to the values can be prepared.

Example 16

<Tg-Max Change Resulting from Concentration Change>

Figure 3:
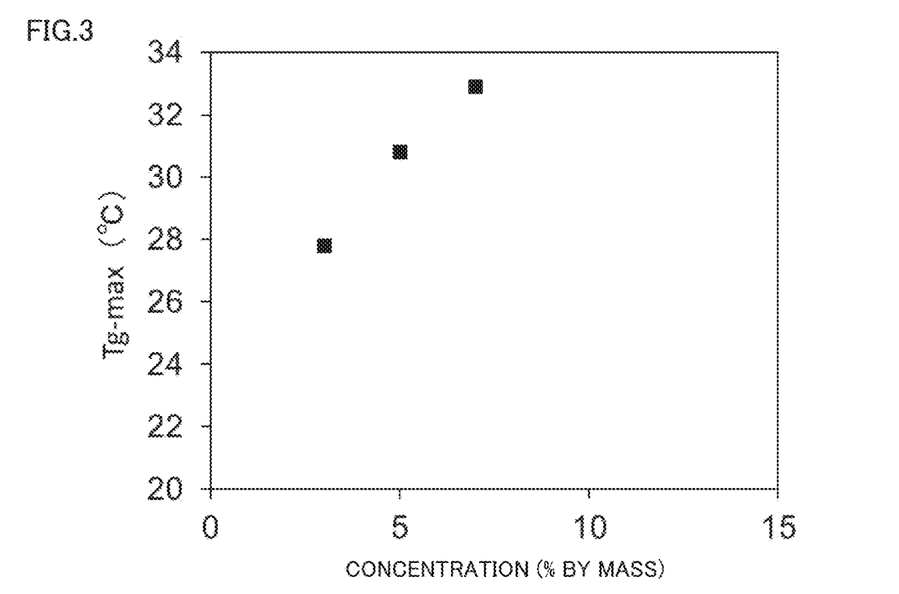
FIG. 3 shows a relation between the gelatin concentration and the Tg-max of the aqueous composition in Example 16.

The gelatin of Example 4 was dissolved in phosphate buffered saline to prepare aqueous solutions containing 3, 5 and 7% by mass of a gelatin. The Tg-max for each of the aqueous solutions was measured. FIG. 3 shows a graph in which a relation between the concentration and the Tg-max is plotted. In the gelatin of Examples 4, the Tg-max increased as the gelatin concentration increased.

Example 17

<Succinylation of Gelatin>

When the high-molecular weight component content is increased, solubility of an aqueous composition containing 5% by mass of a gelatin may decrease. It is generally known that the solubility increases when a gelatin is succinylated, and bulky succinic acid is introduced in a basic amino acid (lysine). Therefore, the gelatin of Example 2 was succinylated.

To a 0.1% aqueous collagen solution as a gelatin raw material kept at a temperature lower than 10° C. in an ice bath, a 1 N aqueous sodium hydroxide solution was added to adjust the pH of the solution to 9 to 10. Pellet-shaped succinic acid anhydride (manufactured by Tokyo Chemical Industry Co., Ltd.) was poured into the aqueous collagen solution in small portions with stirring, and the pH of the solution was adjusted in the range of 9 to 10 by dropping a 1 N aqueous sodium hydroxide solution. All the predetermined amount of succinic acid anhydride was poured into the solution, and the reaction was completed after the pH change was stopped (the reaction time did not exceed 4 hours). By dropping 1 N hydrochloric acid to the obtained reaction liquid, the pH of the liquid was adjusted to around 4, and succinylated collagen was precipitated. The reaction liquid was subjected to centrifugal separation using a centrifugal separator (manufactured by Hitachi Koki Co., Ltd., type: himacCR-GIII) at 4000 rpm for 20 minutes, and a precipitate was collected. After the precipitate was dispersed in diluted hydrochloric acid at pH 4, and washed by centrifugal separation twice, the precipitate was dispersed in pure water to give a dispersion having a precipitate concentration of about 0.1%, and the pH of the dispersion was neutralized by dropping a 1 N aqueous sodium hydroxide solution to dissolve the precipitate. The obtained aqueous solution was dialyzed against pure water in a refrigerator to obtain succinylated collagen as a gelatin raw material.

Figure 4:
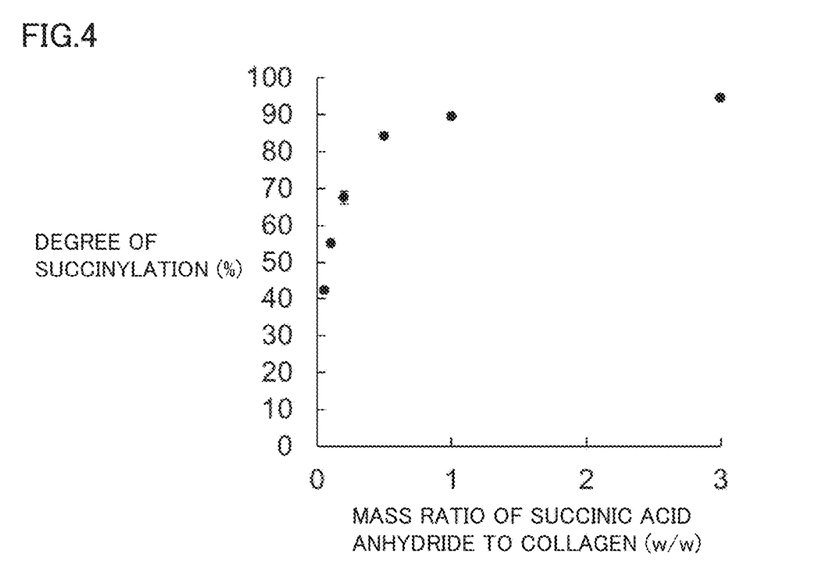
FIG. 4 shows a relation between the mass ratio of a succinic acid anhydride to a gelatin and the substitution rate of a succinylated basic amino acid in Example 17.

In order to control the degree of succinylation, the above succinylation operation of collagen was performed at various ratios of succinic acid anhydride/collagen (w/w) of 0.05, 0.1, 0.2, 0.5, 1, and 3 to prepare a gelatin in the same manner as in Example 1. FIG. 4 shows a relation between the mass ratio of a succinic acid anhydride to a gelatin used in the reaction and the substitution rate of a succinylated basic amino acid. The result shows that the substitution rate reaches a limit at 90%, and further succinylation is not easy.

For a succinyl product of a gelatin having various substitution rates obtained by the reaction, the Tg-max of an aqueous composition containing 5% by mass of the gelatin is measured. The Tg-max of an aqueous gelatin composition having a substitution rate of 40 to 70% is equal to that of an aqueous composition containing the unsubstituted gelatin of Example 2. However, the Tg-max of an aqueous gelatin composition having a substitution rate greater than or equal to 80% is lower than that of the aqueous composition containing the unsubstituted gelatin of Example 2, and a further increase in the substitution rate results in a further decrease in the Tg-max.

Example 18

<Gelatinization Behavior of Aqueous Gelatin Composition>

Figure 5:
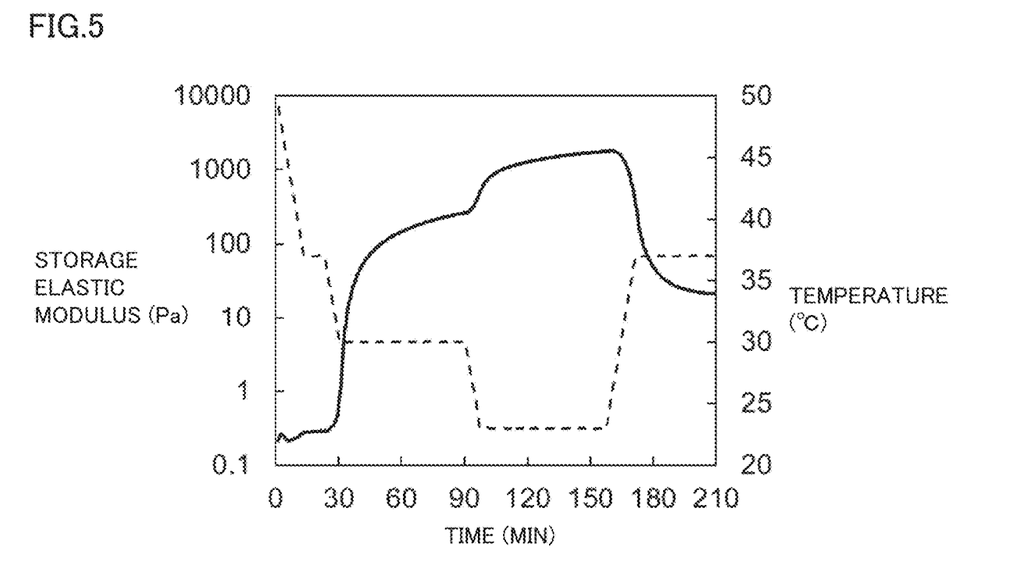
FIG. 5 shows a gelatinization behavior of an aqueous gelatin composition in Example 18.
Figure 6:
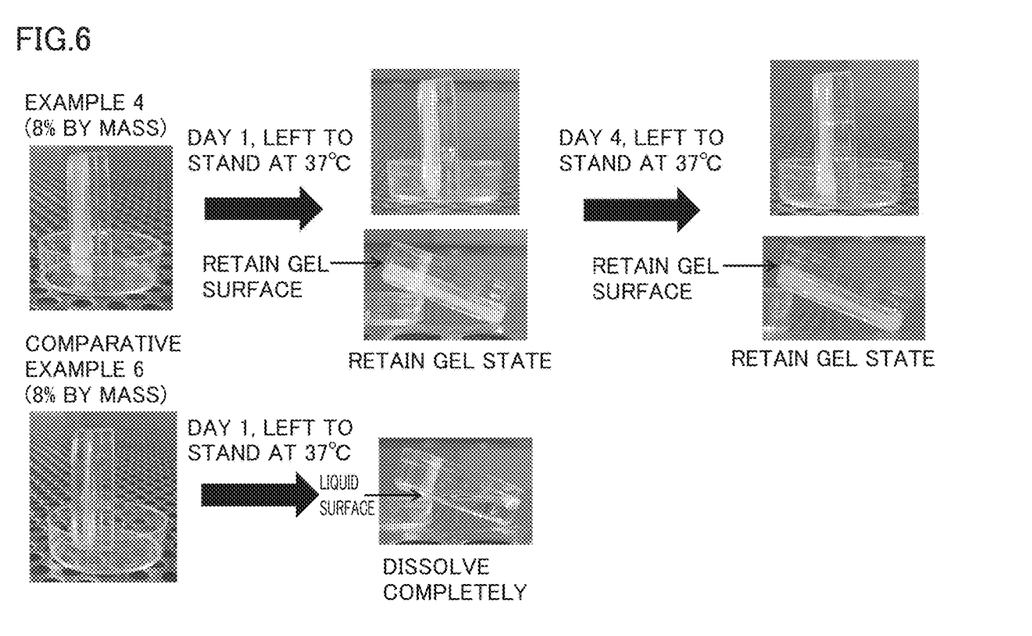
FIG. 6 shows a state of gels of a high-concentration aqueous gelatin composition in Example 20.

An aqueous composition containing 5% by mass of the gelatin of Example 4 was kept warm at varied temperatures of 37° C., 30° C., 24° C., and 37° C. as shown in FIG. 5. The storage elastic modulus G' (Pa) at each of the temperature points was measured using a dynamic viscoelasticity measuring device. FIG. 5 shows the behaviors of the warming temperature and the storage elastic modulus G' (Pa).

At 30° C., the storage elastic modulus G' (Pa) suddenly increased and the aqueous composition was gelatinized, and when the warming temperature was decreased to 24° C., hardness of the gel was further increased. The gel that was formed in this way dissolved quickly at 37° C.

Example 19

<Preparation of Medical Laminate>

Human neonatal skin fibroblast cells NB1RGB (provided by RIKEN BioResource Center, Resource No. RBRC-RCB0222) were cultured on a temperature-responsive cell cultureware until the cells became overconfluent to prepare a cell sheet. An aqueous composition containing 5% by mass of the gelatin of Example 2 was heated to 37° C., added on the cell sheet kept warm at 30° C., and gelatinized to form a first support layer. Next, after the cell sheet and the first support layer were left to stand at room temperature for 30 minutes, they were separated from the cultureware and turned over, and a second support layer was formed on the back surface similarly.

Meanwhile, an aqueous composition containing 5% by mass of the gelatin of Comparative Example 6 was heated to 37° C., and added on the cell sheet kept warm at 30° C., but the aqueous composition was not gelatinized at 30° C. Then, when the aqueous composition was cooled to a temperature lower than 27° C., the cell sheet was not collected since it was separated before starting gelatinization.

<Evaluation of Cell Viability of Cells Isolated from Medical Laminate Stored at Room Temperature Using Hemocytometer>

The medical laminate prepared in Example 19 was left to stand at room temperature, cells were collected from the medical laminate, and the cell viability of the cells was measured. Table 3 shows the results. A cell viability greater than or equal to 95% was shown until day 3 after the cell collection, and a cell viability greater than or equal to 90% was shown on day 7 after the cell collection.

TABLE 3

| | Stationary period (day) | | | | |
|---|---|---|---|---|---|
| | 0 | 1 | 2 | 3 | 7 |
| Cell viability (%) | 99.3 ± 0.5 | 96.4 ± 3.7 | 96.3 ± 0.4 | 98.2 ± 1.8 | 92.0 ± 10.2 |

Example 20

<High-Concentration Aqueous Gelatin Composition>

The gelatin of Example 4 was dissolved in phosphate buffered saline to give a solution containing 8% by mass of the gelatin, and 2 mL of the solution was added to a 35 mm culture plate. The solution was left to stand at 20° C. overnight and gelatinized. Then, the solution was incubated at 37° C., and observed on day 1 and day 4 after the incubation. In addition, similarly, a solution containing 8% by mass of the gelatin of Comparative Example 6 was prepared, left to stand at 20° C. overnight, and gelatinized. Then, the solution was incubated at 37° C., and observed on day 1 after the incubation. FIG. 7 shows states of both the gels.

It is found that the gel of 8% by mass of the gelatin of Comparative Example 6 was dissolved at 37° C. on day 1, whereas the gel of 8% by mass of the gelatin of Example 4 sufficiently remained in the gel state at 37° C. even on day 4. By using the properties that the gelatin of the present invention does not melt at 37° C., the gelatin can be applied to various uses such as culture media, food, cosmetics, and medicine in addition to a cell sheet.

An aqueous composition prepared by mixing the gelatin of the present invention with water is gelatinized rapidly at a temperature greater than or equal to 27° C., and undergoes dissolution from a gel state at a temperature greater than or equal to about 32° C. Based on this effect, the present invention can be used for storage and transfer of a cell sheet.

The invention claimed is:

1. A gelatin or a chemically modified product thereof, comprising 10 to 50% by mass of a high-molecular weight component having a molecular weight higher than that of a γ-chain, and a low-molecular weight component having a molecular weight lower than that of an α-chain in such an amount that a value obtained by subtracting the low-molecular weight component content from the high-molecular weight component content is greater than or equal to 0% by mass, wherein
the gelatin or the chemically modified product thereof comprises 1.6 to 9.6% by mass of the low-molecular weight component.

2. The gelatin or the chemically modified product thereof according to claim 1, which is derived from tendon-derived collagen.

3. A method for producing the gelatin or the chemically modified product thereof according to claim 1, comprising:
adding collagen to water to give a solution having a collagen concentration of 0.1 to 10% by mass;
adjusting pH of the solution to 2 to 9; and
thermally denaturing the collagen at a temperature in a range of 40° C. to 80° C.

4. The method according to claim 3, wherein the collagen is derived from a tendon.

5. An aqueous composition, comprising the gelatin or the chemically modified product thereof according to claim 1 in an amount of 0.5 to 10% by mass.

6. A medical laminate, comprising a cell sheet, and one or two support layers containing the gelatin or the chemically modified product thereof according to claim 1 adhering to one or both surfaces of the cell sheet.

7. A method for producing a medical laminate, comprising:
coating a cell sheet formed on a culture substrate with a liquid aqueous composition or sol-like aqueous composition containing the gelatin or the chemically modified product thereof according to claim 1; and
gelatinizing the liquid aqueous composition or sol-like aqueous composition on the cell sheet to form a support layer to thereby produce a medical laminate.

8. A method for isolating a cell sheet, comprising:
coating a cell sheet formed on a culture substrate with a liquid aqueous composition or sol-like aqueous composition containing the gelatin or the chemically modified product thereof according to claim 1,
gelatinizing the liquid aqueous composition or sol-like aqueous composition on the cell sheet to form a support layer,
and medical laminate, and
removing the gelatinized support layer comprising the cell sheet from the medical laminate to isolate the cell sheet.

* * * * *

UNITED STATES PATENT AND TRADEMARK OFFICE
CERTIFICATE OF CORRECTION

PATENT NO. : 10,815,393 B2
APPLICATION NO. : 15/769362
DATED : October 27, 2020
INVENTOR(S) : Yoshimi Ohyabu et al.

It is certified that error appears in the above-identified patent and that said Letters Patent is hereby corrected as shown below:

Claim 8, Line 8, should read as follows:
8. A method for isolating a cell sheet, comprising:
coating a cell sheet formed on a culture substrate with a
    liquid aqueous composition or sol-like aqueous com-
    position containing the gelatin or the chemically modi-
    fied product thereof according to claim 1,
gelatinizing the liquid aqueous composition or sol-like
    aqueous composition on the cell sheet to form a support
    layer
and medical laminate, and
removing the gelatinized support layer comprising the cell
    sheet from the medical laminate to isolate the cell sheet.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*